United States Patent [19]

Andreussi

[11] Patent Number: 5,064,417

[45] Date of Patent: Nov. 12, 1991

[54] DEVICE FOR FASTENING A CATHETER TO A CRANIAL THECA FOR PERFORMING CEREBRO SPINAL FLUID DRAINAGE TO THE OUTSIDE OPERATIONS

[75] Inventor: Luciano Andreussi, Cagliari, Italy

[73] Assignee: Co Pharma Corporation S.R.L., Genoa, Italy

[21] Appl. No.: 420,093

[22] Filed: Oct. 11, 1989

[30] Foreign Application Priority Data

Oct. 11, 1988 [IT] Italy .................... 22259A/88

[51] Int. Cl.⁵ .................................... A61M 5/00
[52] U.S. Cl. ........................................... 604/175
[58] Field of Search ............. 604/8, 9, 174–180, 604/905, 283; 128/DIG. 26; 623/11, 12, 66

[56] References Cited

U.S. PATENT DOCUMENTS

| | | | |
|---|---|---|---|
| 3,540,451 | 11/1970 | Zeman | 604/8 |
| 3,685,680 | 8/1972 | Tenckhoff et al. | 604/29 |
| 3,788,327 | 1/1974 | Donowitz et al. | 604/175 |
| 4,781,694 | 11/1988 | Branemark et al. | 604/175 |
| 4,813,967 | 3/1989 | Renard et al. | 623/66 |

FOREIGN PATENT DOCUMENTS 699253  11/1953  United Kingdom ....... 128/DIG. 26

Primary Examiner—John D. Yasko
Assistant Examiner—Anthony Gutowski
Attorney, Agent, or Firm—Darby & Darby

[57] ABSTRACT

A device for fastening a catheter to an osteofibrous wall, for example, to a cranial theca (6) for draining cerebro spinal fluid or any other serous fluid therefrom, particularly for use in pediatric neurosurgery, comprising a tubular body (1) arranged to receive a catheter (10), at least one transverse end foot (2) for insertion into an aperture (7) in the cranial theca (6), and a locking element (4) which can be fitted in opposite relationship with the foot (2) so as to bear on the outer surface of the cranial theca (6) in close liquid-tight contact therewith.

4 Claims, 1 Drawing Sheet

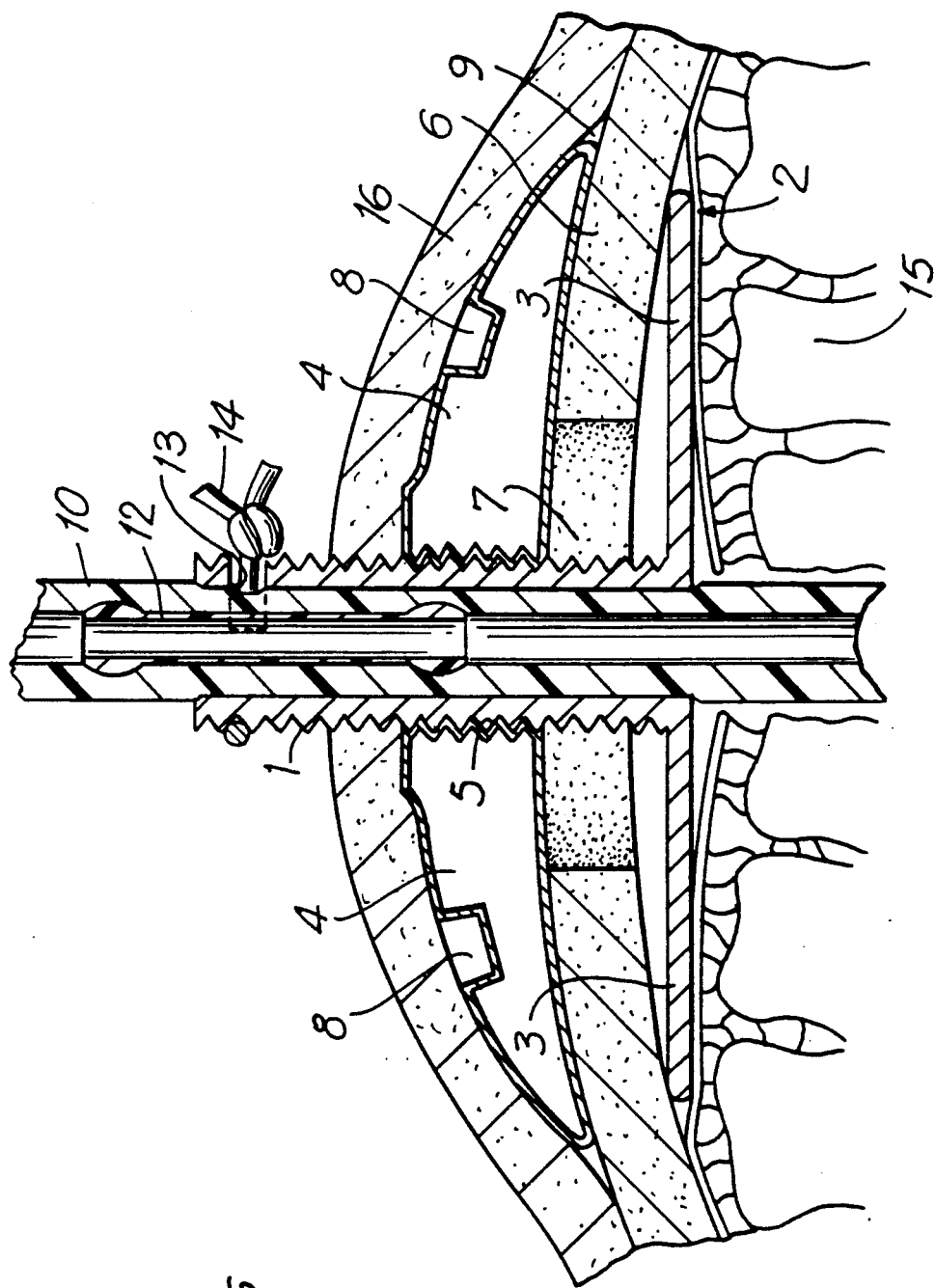
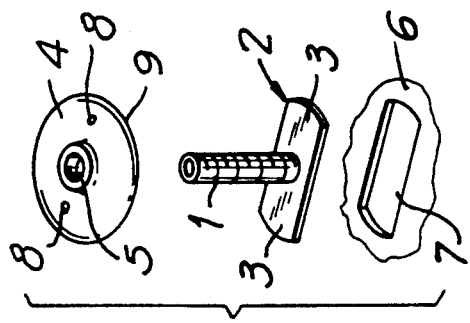

DEVICE FOR FASTENING A CATHETER TO A CRANIAL THECA FOR PERFORMING CEREBRO SPINAL FLUID DRAINAGE TO THE OUTSIDE OPERATIONS

BACKGROUND OF THE INVENTION

1. Field of the Invention

This invention relates to a device for fastening a catheter to a cranial theca for performing cerebro spinal fluids drainage to the outside operations, particularly as practiced in pediatric neurosurgery.

2. Description of the Related Art

It is known to those skilled in the art of neurosurgery that in order to treat hydrocephalic patients, a catheter is introduced into the patient's cranial theca for effecting draining of cerebro spinal fluid therefrom, and that such cerebro spinal fluid external drainage may have to be extended in time over many weeks under some circumstances.

At present, in pediatric neurosurgery, particularly when operating on children less than three years old, whose cranial theca is thin, it is a current practice to simply insert a catheter into a hole formed in the bone and to retain the catheter in position by passing it through a subcutaneous tunnel.

This system of cerebro spinal fluid external drainage as used in pediatric neurosurgery has great disadvantages particularly in that poor tightness between the catheter and the hole in the cranial theca results in leaking out of cerebro spinal fluid and the risk of severe infections, especially when the drainage to the outside has to be extended in time.

Thus, cerebro spinal fluid fistulae are often produced because of the cutaneous and subcutaneous tissues and the theca bone being thin and distrophic in nature.

SUMMARY OF THE INVENTION

It is an object of this invention to eliminate the above-mentioned disadvantages by providing a device for fastening a proximal, ventricular catheter which can achieve firm securing in place of said catheter, optimal liquid-tight seal at the cranial theca-ventricular catheter junction, as well as permit a cerebro spinal fluid drainage to the outside to be extended in time over many weeks, where necessary.

The fastening device according to the invention substantially comprises a tubular body provided at one end with at least one foot consisting of two transverse projections which, when in use, are opposite to one another, and a locking element that can be fitted around the tubular body to cooperate with said transverse foot in firmly locking the tubular body in position.

According to a preferred embodiment of the invention, said tubular body is a hollow screw having a lumen into which a catheter can be inserted to a desired length; the transverse foot consists of two oppositely arranged tongue portions integral with said hollow screw and orthogonally jutting out with respect to the axis of the screw, while said locking element is a nut taking the form of a concave disc the concavity of which is directed towards the transverse foot.

In order to install the fastening device according to the invention, first an elongated craniectomy is formed into patient's cranial theca with the large dimension of this aperture being smaller than the length of the transverse foot so as to allow the foot to be inserted by a swinging movement thereof. Following to insertion, the axis of the screw is rotated by 90° as a result of which the transverse foot will be oriented in the direction of the small dimension of the elongated craniectomy such that the foot can firmly engage the inside walls of the skull. Then the concave disc is fitted in place by threadingly engaging it around the screw from the outside until the peripheral edge of the disc is brought into close contact with the bone surface, thereby to ensure an optimal tightness condition.

A catheter can be inserted into the lumen of the hollow screw either before or after fitting in place of the screw, by the catheter being gently stretched on a stylet in such a manner that, upon withdrawing of the mandrel, the catheter, which is of a resilient plastics material, will closely adhere to the internal wall of the screw, to thereby ensure tightness.

In order to further increase tightness between the screw inside surface and the catheter, a resilient tubular element can be, again by means of a mandrel, introduced into catheter so that the inserted tubular element will urge the wall of the catheter against the internal surface of the screw. Moreover, a groove is made on the screw and a surgical silk thread tied through the groove.

Providing the transverse foot integral with the screw body has proven to be a most satisfactory solution but it will be understood that a movable foot may also be provided. By way of example, one of the two foot tongue portions may be arranged to be rotatable so that as the screw is being inserted into the elongated carniectomy the rotatable tongue is moved to a position where it is superposed upon the other tongue and thereafter it is rotated to an opposite position thereto. Also, more than one transverse foot may be provided.

The fastening device for catheter according to the invention can also be used in experiments on animals provided with a cranial theca being quite thin in thickness, as well as for securing a catheter to other fibrous walls, such for example an abdominal wall.

BRIEF DESCRIPTION OF THE DRAWINGS

A device for fastening a catheter according to the invention will now be described in relation to one preferred embodiment thereof, reference being made to the accompanying drawing, in which:

FIG. 1 is an axonometric exploded view of a fastening device according to the invention, the figure also showing a portion of cranial theca having an aperture for receiving the foot of the device, FIG. 2 is a median sectional view of the device in FIG. 1 when in a condition of use.

DETAILED DESCRIPTION OF THE PREFERRED EMBODIMENTS

Referring now to the above figure, a device for fastening a catheter for use in cerebro spinal fluid ventricular external drainage according to this invention, substantially comprises a hollow screw 1 having at one end a foot 2 integrally formed with the screw 1 and consisting of two oppositely arranged tongue portions 3 orthogonally oriented with respect to the axis of screw 1, and a washer means 4 in the form of a concave disc 4 having a threaded central hole 5 whereby the disc 4 can be threadingly engaged on the screw 1 from the opposite end to the foot 2 with the concavity of the disc 4 being directed towards the foot 2.

In order to install the device according to the invention in a cranial theca 6 of a patient, particularly of a child less than three years in age, an elongated aperture 7 is formed in the cranial theca 6 with the small dimension of this aperture 7 being such as to be able to accomodate the foot 2 in a direction of width thereof, while the large dimension of aperture 7 is preferably smaller than the full length of foot 2 but such as to permit the foot 2 to be passed through the aperture 7 by first introducing one tongue portion 3 of the foot and then the other one; this with the purpose of reducing to as small as possible the size of aperture 7 as compared with that of foot 2.

Once the foot 2 has been inserted in the aperture 7, the screw 1 is rotated by 90° so that the foot 2 will be oriented in the direction of small dimension of aperture 7, whereby the foot tongue portions 3 will rest against the internal walls of the cranial theca 6, as clearly shown in FIG. 2, without said tongue portions 3 being allowed to become released therefrom.

Then, the concave disc 4 is threadingly engaged onto the screw 1—if necessary, by using a surgical pince to take hold on two dead holes 8 provided to this end in the convex face of disc 4—until at least the peripheral edge 9 of disc 4 is brought into close contact with the bone surface, thereby providing a good tightness (see FIG. 2).

The proximal, ventricular catheter shown by reference numeral 10 in sectional view FIG. 2, can be inserted into the lumen 11 of hollow screw 1 either before or following installation of the screw in the cranial theca 6. To this purpose, the catheter can be gently stretched on a mandrel so that upon withdrawing of the mandrel, the catheter will closely adhere to the internal surface of screw 1 under springback effect of the catheter plastics material. Thus, a good tightness can be obtained.

In order to further increase sealing contact between the internal face of hollow screw 1 and the catheter 1, a tubular resilient element 12 (see FIG. 2) can be, by means of a second mandrel, introduced into the catheter 10 whereby to urge the catheter 10 against the internal surface of the screw.

Furthermore, a circumferential cut 13 can be made to extend over an arc of 160° on the screw 1 and a surgical silk thread 14 can be tied at the level of this cut, as shown in FIG. 2, to further increase tightness of the system.

Installation of the fastening device according to the invention for fastening a catheter to a cranial theca of a patient, should be apparent from the sectional view in FIG. 2 where schematically shown, at 15, is the cerebral matter within the cranial theca 6 and, at 16, the scalp covering the disc 4 after installation; FIG. 2 clearly shows the good liquid-tight seal which is provided at the cranial theca-ventricular catheter junction.

As a result of this good tightness, the risk of any liquid leaking out can be entirely prevented.

This permits the fluid drawing-off operation to be extended in time over many weeks, where necessary, without any risk of infection or formation of serous fluid fistulae being incurred.

Conveniently, the fastening device according to the invention can be entirely produced from Teflon which is known as a neutral material. However, utilization of such materials as for example carbon fibers or even biopolymer materials is not excluded. Biopolymer materials are known as having a tendency to be penetrated by bone tissue to become amalgamated therewith; thus, when the device of the invention is made from biopolymers it can permanently remain absorbed in the cranial theca by the process of reossification.

While in this disclosure the foot 2 is described as being integral with the screw 1, it is to be understood that the foot 2 could be designed in other ways. Thus, according to an advantageous embodiment, one of the tongue portions 3 is integral with the screw 1 while the other portion 3 is arranged to be rotatable around the screw 1, in such a manner that, before the foot 2 is inserted into the aperture 7, this rotatable tongue 3 can be moved to a position where it is superposed on the fixed tongue and, thereafter, to a position opposite to said fixed tongue. This permits the aperture 7 to be further reduced in size.

Likewise, there may be more than one foot 2 and, for example, two feet 2, may be provided so that one of them is rotatable and can be rotated to a position where it is either superposed upon the other foot or placed orthogonally thereto.

Also, it is to be emphasized that although the fastening device of the invention is particularly intended for use in pediatric neurosurgery operations, it could be utilized as well in experimental work on animals, particularly animals having a cranial theca rather thin in thickness, for drawing-off cerebrospinal fluid, or making drug infusions, or the like.

Again, the method of fastening catheters according to the invention can be applied for securing catheters to fibrous walls, such as abdominal walls.

While the invention has been particularly described hereinabove and shown in the accompanying drawings in relation to a specific embodiment thereof, it is to be understood that many changes may be made to the details of construction without departing from the spirit and scope of the invention as defined in the appended claims.

Moreover, it must be emphasized that the invention herein described works actually as an access to the cerebro spinal fluid spaces. Therefore, the described device is a tool suitable for any perfusion and installation or drainage to the outside of any possible fluid containing medications.

I claim:

1. A device for fastening a catheter to a cranial theca, particularly for use for ventricular cerebro spinal fluid drainage to the outside in pediatric neurosurgery, comprising:
   a screw having a lumen for receiving a catheter;
   at least one transverse foot provided at a first end of said screw and arranged to be received and locked in place in an aperture in the cranial theca;
   said foot having a length greater than its width, the length of said foot being greater than a length and a width of the aperture, and means for rotating said foot after insertion into the aperture; and
   a means for locking said screw in place, said locking means fitted on a second end opposite said first end of said screw to bear on an outer surface of the cranial theca in liquid-tight contact, said locking means being a nut in the form of a concave disc, the concavity of which is directed towards the foot, and said disc having a central threaded hole to threadingly engage the screw.

2. The device according to claim 1, wherein two diametrically opposite dead holes are provided on a convex surface of said disc and permit the disc to be engaged and disengaged by the aid of a surgical pincer.

3. The device according to claim 1, further comprising a tubular resilient element for placement within the inside of the catheter for urging the catheter against an internal wall of said screw.

4. The device according to claim 2, wherein said foot is integral with the screw and comprises two oppositely disposed tongue portions orthogonally oriented relative to an axis of the screw.

* * * * *